United States Patent [19]
Pienkowski et al.

[11] Patent Number: 5,879,388
[45] Date of Patent: Mar. 9, 1999

[54] IMPLANT PRE-TREATED FOR REDUCING THE GENERATION OF WEAR PARTICULATES

[75] Inventors: David A. Pienkowski; Kwon-Yong Lee, both of Lexington, Ky.

[73] Assignee: The University of Kentucky Research Foundation, Lexington, Ky.

[21] Appl. No.: 963,057

[22] Filed: Nov. 3, 1997

Related U.S. Application Data

[60] Division of Ser. No. 639,579, Apr. 29, 1996, Pat. No. 5,709,020, which is a continuation-in-part of Ser. No. 276,972, Jul. 19, 1994, Pat. No. 5,515,590.

[51] Int. Cl.⁶ ........................................................ A61F 2/32
[52] U.S. Cl. ................................ 623/18; 623/22; 623/901
[58] Field of Search .................................. 623/18, 19, 20, 623/21, 22, 23, 901; 29/404

[56] References Cited

U.S. PATENT DOCUMENTS 5,037,928  8/1991  Li et al. ........................................ 623/22

OTHER PUBLICATIONS

Mckellop, et al.; "Friction and Wear Properties of Polymer, . . . on a Multichannel Screenig Device"; J of Biomedical Materials Research; 15, 619–653; (1981).

Murall Jasty; "Clinical Reviewa: Particulate Debris and Failure of Total Hip Replacements"; Journal of Applied Biomaterials; 4, 273–276; (1993).

Dowson, et al.; "Wear Particles: From the Cradle to the Grave"; The Institute of Tribology, Leeds University; Tribology Series, 21; Symposium Sep. 1991.

"The Osteolysis Challenge"; Orthopaedic Insight; vol. 1, No. 3; Feb. 1994.

"Arcom Processed Polyethylene, Uniform Compression Molded: Test Results"; Biomet, Inc. (1993).

Peinkowski, D. et al., ; Low–Voltage Sanning Election Microscope Imaging of Ultrahogh–Molecular–Weight Poly– Ethylene; J. of Bio. Mat. Res. ; VO. 29; 1995; 1167–74.

Pleskachevsky et al.; Oxidation and Its Influence on Low Pressure Polyethylene Wear; Wear; 181–183; 1995; 222–6.

*Primary Examiner*—David P. Bryant
*Attorney, Agent, or Firm*—King and Schickli

[57] ABSTRACT

A method is provided for reducing the amount of wear particulates generated by a total joint orthopaedic implant. The implant consists of two matched articulating components wherein at least one of the components is made of polymer or other material with similar physical properties. The method includes the steps of placing the total joint orthopaedic implant in a fluid bath and articulating the implant in the fluid bath for at least 1,000 cycles. The articulation may be performed in three stages. In the first, the implant is articulated under a load of substantially 0.1–500 Newtons with sliding speeds of substantially 0.01–0.5 meters per second. During a second stage the articulation takes place under a load of substantially 100–2,500 Newtons with sliding speeds of substantially 0.01–0.5 meters per second. In the third stage the articulation takes place under a load of substantially 2,500–10,000 Newtons at sliding speeds of 0.5–2.0 meters per second. The method also includes pre-implantation creeping for the polymer component. This improves the wear resistance of the polymer component, as well as, increases the conformity between the matched articulating components resulting in reduced wear particulate generation.

8 Claims, 1 Drawing Sheet

IMPLANT PRE-TREATED FOR REDUCING THE GENERATION OF WEAR PARTICULATES

This is a division of U.S. patent application Ser. No. 08/639,579, filed Apr. 29, 1996, now U.S. Pat. No. 5,709,020, which is a continuation-in-part of U.S. patent application Ser. No. 08/276,972, filed on Jul. 19, 1994, now U.S. Pat. No. 5,515,590.

TECHNICAL FIELD

The present invention relates generally to the field of orthopaedic implants and, more particularly, to a method for reducing the amount, or modifying the shape or size of wear particulates generated by a total joint orthopaedic implant following implantation in a patient.

BACKGROUND OF THE INVENTION

Each year approximately 500,000 human joints require replacement as a result of debilitating disease or damage from an accident. Hip and knee joints represent a majority of these. To meet this need, a variety of total joint orthopaedic implants have been designed and are presently being marketed by various manufacturers. Examples of these are shown, for example, in U.S. Pat. Nos. 5,021,063 to Tager; 5,030,238 to Nieder et al.; 5,108,452 to Fallin; and 5,180,394 to Davidson.

Total joint orthopaedic implants are composed of two articulating components. The first of these components includes a concave surface made from a polymer or a ceramic (usually the former). The second of these components includes a convex counterface, typically formed of either metal or ceramic that is designed to slide or roll over the polymer or ceramic surface.

Ultrahigh molecular weight polyethylene remains the dominant polymer for utilization in the construction of concave bearing surfaces in total joint orthopaedic implants at the present time. To prevent undue wear to this bearing surface, the hard metal or ceramic counterface of the other component of the total joint orthopaedic implant should have an exceptionally smooth surface as roughness is directly related to the wear rate. The average surface roughness of, for example, a hip joint is about 0.025 $\mu$m. It should be appreciated, however, even such a smooth hard, metal or ceramic surface generates wear particulates from the softer polymer surface. These wear particulates, unfortunately have been shown to be associated with adverse tissue reactions over time.

Specifically, the wear particulates stimulate cellular activity in the form of an immune system response. More specifically, inflammation and foreign body reactions result including macrophage and foreign body giant cell activity. This process leads to the production of bone resorbing cytokines (e.g. IL-1, IL-6, P6E-2, etc.) which lead to destruction of the bone tissue holding the implant securely in place. These conditions likely contribute to the loosening of prosthetic components eventually resulting in pain and failure of the total joint orthopaedic implant.

The shape, size and volume of the wear particulates produced may determine the type and extent of the adverse tissue and cellular reactions that are stimulated. It is hypothesized that very small wear particulates are transported away from the implant site and eliminated by the lymphatic system. More specifically, these very small particulates are phagocytized and transported through the lymphatic system by macrophages. The volume or rate of the particulates that the macrophages can phagocytize and transport, however, may be less than the volume or rate of particle generation. Furthermore, this volume or rate may depend upon the material composition of these small particulates, as well as their shape or size. Accordingly, the lymphatic system may become overloaded as a result of increased wear rates with the resulting particulate generation leading to an accumulation of wear particulates in the tissues around the total joint orthopaedic implant. This may produce a chronic inflammatory response that eventually leads to bone resorption.

Although larger wear particulates generally remain in the tissue surrounding the implant, they also can produce a chronic foreign body response which may eventually give rise to bone resorption. Accordingly, it should be appreciated that wear particulates have been repeatedly associated with aseptically loosened implants, a condition that eventually requires total joint orthopaedic implant replacement surgery. A need is therefore identified for a procedure to reduce the number, or modulate the shape and size of wear particulates generated in a human from a total joint orthopaedic implant. By successfully addressing this need, it is possible to increase the service life of the total joint orthopaedic implant and thereby reduce the need for difficult, painful and costly revision surgery.

Recognizing the problem resulting from wear particulate generation, a number of solutions have been proposed. As set out in the article entitled "Clinical Reviews: Particulate Debris And Failure of Total Hip Replacements" by Murali Jasty in the *Journal of Applied Biomaterials*, Volume 4, pp 273–276 (1993), these approaches include: the use of polyethylene components with more than 8 mm wall thickness and the use of head sizes smaller than 32 mm; the use of non-titanium alloys; the use of circumferential porous coatings on the femoral components; the use of prosthetic designs and surgical techniques to obtain rigid initial fixation at surgery, the minimizing of the modularity of the components and the surface hardening of the metal surface with techniques such as nitrating or ion implantation.

While each of these approaches is successful to some degree, none is directed to removing laps, folds and other surface irregularities (which form wear debris and would otherwise be produced in the body after implantation) prior to the implanting of the total joint orthopaedic implant into a patient. Further, while some clinical studies of the generation of wear particulates in a total joint implant have been completed and still others are ongoing, there has been absolutely no suggestion in the art that any method could be utilized to pre-wear a pair of matched implant joint bearing surfaces prior to implantation so as to significantly reduce the amount, rate of generation, or change the shape or size of wear particulates generated following implantation and thereby increase the service life of the total joint orthopaedic implant.

In addition, none of the known approaches are directed to increasing the conformity between the bearing surfaces of the articulating components which comprise the total joint orthopaedic implant. Particularly, there is no suggestion in the art that a method of pre-loading a pair of matched implant joint bearing surfaces, either above or with a pre-wearing process could be utilized to increase the conformity and to reduce the amount or change the shape or size of wear particulates generated following implantation and thereby increase the service life of the total joint orthopaedic implant.

SUMMARY OF THE INVENTION

Accordingly, it is a primary object of the invention to provide a method for reducing the amount, rate of generation, or changing the shape and size, of wear particulates generated by a total joint orthopaedic implant following implantation so as to thereby effectively reduce the resulting stimulation of the immune system of the patient. In this way, potent bone resorbing cytokines are not as actively stimulated by these wear particulates, the implant remains firmly attached to the bone, and a longer implant service life is provided.

Yet another object of the invention is to provide a relatively simple, inexpensive and easily completed method for the pre-breaking-in or pre-wearing of a total joint orthopaedic implant consisting of two matched articulating components. Specifically, the components are articulated in a cyclical manner to remove laps, folds, and other surface irregularities prior to implantation. These laps, folds and irregularities would otherwise lead to the production of wear debris, the stimulation of cytokine release, and ultimately, contribute to the loosening and failure of the implant.

Yet another object of the present invention is to provide an improved method for substantially reducing the amount or volume of wear particulates generated by a total joint orthopaedic implant following implantation wherein the implant is pre-worn to remove laps, folds, and other surface irregularities and provide good component-component fit and bearing surface polish. Further, the implant bearing surfaces could also be conditioned by this process with a film layer so as to significantly reduce the friction, wear particle generation and wear particle burden imposed by the implant on surrounding tissue following implantation. Advantageously, this effectively increases the overall service life of the implant, not only serving to reduce the inflammation and pain associated with total joint implants in the past, but also in many cases substantially postponing or altogether eliminating the need for subsequent revision/replacement surgery.

Another object of the present invention is to provide a relatively simple, inexpensive and effective method of pre-implantation creeping for increasing the conformity between the bearing surfaces of the articulating components which make up the total joint orthopaedic implant. Specifically, by increasing the conformity, the wear particulate generation is reduced following implantation and thereby the service life of the implant is increased.

Still another object is to provide, for example, can acetabular cup or tibial component of a total joint orthopaedic implant, or in general, the concave polymer surface thereof subjected to pre-implantation creeping in order to increase conformity between the bearing surfaces of the articulating components thereby reducing wear particulate generation after implantation and consequently increasing the service life of the implant.

Additional objects, advantages and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, and in accordance with the purposes of the present invention as described herein, an improved method is provided for reducing the amount or volume of wear particulates generated by a total joint orthopaedic implant, including an acetabular cup with concave polymer surface and matching convex counterface of metal or ceramic after it is implanted in the body of a patient. More specifically, the method includes the step of placing the total joint orthopaedic implant, consisting of these two matched articulating components, in a fluid bath so that the implant is completely submerged in the fluid. Preferably, the fluid has a viscosity between 0.5–2000 times that of water.

The fluid may be selected from a group of fluids having components consisting of water, fetal calf serum, bovine serum, natural or synthetic synovial fluid and any mixtures thereof. The method also includes a step of articulating the total joint orthopaedic implant in the fluid bath, preferably all at a constant temperature, for at least 1,000 and more preferably at least 10,000 cycles whereby the total joint orthopaedic implant is pre-worn outside the body of the patient. This is done to remove laps, folds, and other irregularities that would otherwise be removed and particles generated in the body following implantation where such particles would inflame tissues and stimulate cellular activity and specifically, the immune system of the patient.

Advantageously, by removing a substantial portion of the wear particulates, which have been shown to be generated in greater volume during the earliest cycles of articulation of the total joint implant, and further by providing good surface-to-surface fit and polish the wear particulate burden imposed by the implant on the surrounding tissue is reduced following implantation. As a result, the immune system response in the patient is reduced or possibly eliminated, along with the associated inflammation, bone resorption and pain. Thus, patient comfort is increased. Additionally, as loosening of the implant from the destruction of the supporting bone is stimulated by wear particle mediated cytokine release from the immune system reactions of the patient, the loosening process is slowed thereby increasing the overall service life of the implant. In many applications, the resulting service life of the total joint implant will be extended for a sufficient period of time to allow the patient receiving the implant to avoid the need for revision surgery, thereby significantly reducing health care costs.

In accordance with yet another aspect of the present method, there is the step of establishing a film layer on the total joint orthopaedic implant and particularly, the relative sliding polymer and metal or ceramic weight bearing surfaces. This is done by including film layer forming solutes in the fluid bath. The solutes may, for example, be selected from a group of materials consisting of polytetrafluoroethylene, hyaluronic acid, lubricin, other natural or synthetic solvents or solutes and any mixtures thereof.

In accordance with a still further aspect of the present invention, the fluid from the fluid bath may be drained and replaced concurrently while the articulating and establishing steps are ongoing. Accordingly, as the film layer forming solutes are absorbed and incorporated into the surface of the joint implant, and particularly in the sliding load bearing surface areas, those solutes are replaced. Accordingly, a greater concentration of solutes is available throughout the entire processing period so as to increase the level of absorption into the implant. As a result of lubricant absorption, friction between the wear bearing surfaces is reduced following implantation and the production of troublesome wear particulates is thereby further minimized.

Alternatively, in certain applications and when utilizing the present method to process certain implant materials with certain film layer forming solutes, it may also be desirable to filter the fluid in the fluid bath. In this way, particulates that are generated during the early cycles of articulation are removed from the fluid. As a result of removal by filtration, such particulates are not continually passed through and squeezed between the relative sliding load bearing surfaces of the matched articulating components of the implant where such particulates would otherwise function as a third-body abrasive and further increase particulate generation and destruction of the implant bearing surface. Filtering is in fact a particularly important step of the method during the final stage of articulation wherein the smooth polishing and hardening of the matching load bearing surfaces is an essential aspect of the present invention.

In accordance with yet another aspect of the present invention, the articulating and establishing steps of the method are completed in accordance with specific processing parameters. Preferably, the cycling of the orthopaedic joint implant is completed at between 0.01–100 Hz. Further, there is the loading of the total joint orthopaedic implant so as to carry a time-varying load of between 0.1–10,000 Newtons during articulation. This time variation of load may follow a square, triangular, or sinusoidal loading regime, or a more clinically relevant load profile such as the Paul curve. Most preferably, the loading occurs at the lower end of this range during the initial stages of articulation. This allows wearing in and stripping away of pronounced laps and folds during the initial stages of processing without gouging, scoring, pitting, abrading or otherwise damaging the bearing surfaces. Further, this initial processing may be done dry, in the presence of a very low viscosity lubricant such as water or in the presence of a higher viscosity fluid such as bovine serum.

As the cycling continues, the loading is increased to a level approximately equivalent to the loading expected to be placed upon the implant following implantation in the patient. This allows fine wearing in and some localized surface hardening of the mating load bearing surfaces. Preferably, during this second stage of processing, the method includes a further step of varying the load carried by the total joint orthopaedic implant during articulation to simulate the load expected to be placed upon the implant by a patient during actual use following implantation.

This method also includes a provision for loading the implant using a load and frequency profile that closely matches that load and frequency profile which will be applied by the actual patient into which this specific articulating pair, now being "broken-in" will be surgically implanted. In this way, the implant is pre-worn in a manner that is effectively "customized" to its eventual operative environment so that particulate generation following implantation is absolutely minimized. Typically, this second stage of processing is performed with the implant submerged in a fluid bath having particular solvents, solutes, and physical properties.

In the final stage of processing, loading and sliding speeds are greatly increased to cold work and harden the load bearing surfaces. Simultaneously, solutes present in the fluid bath are forced into and absorbed by these bearing surfaces so as to form a film layer. As a result of the present process, in many cases it is anticipated that particulate generation following implantation will be of a nature in both size, shape and volume so that the macrophages of the patient should be able to successfully phagocytize and transport the resulting particulates through the lymphatic system without activating the cascade of cytokines which destroy bone. In this way, a physiological equilibrium is achieved and the service life of the implant is significantly extended. As a result, inflammation and pain are also substantially eliminated. Accordingly, this invention represents a significant advance in the art.

In accordance with still another important aspect of the present invention, a pre-broken-in or pre-worn total joint orthopaedic implant is provided in accordance with the present method.

In accordance with yet another important aspect of the invention, the method may include the step of subjecting the acetabular cup or socket of the total joint orthopaedic implant to pre-implantation creeping. More specifically, the pre-implantation creeping utilizes the visioelastic properties of the polymeric material to increase the conformity between the polymer concave surface of the socket and the convex counterface component, which is preferably formed of either metal or ceramic that is adapted to slide or roll over the polymer surface. Conformity designates how well the mating surfaces of the polymer concave component and the convex counterface component fit together. When there is a lack of conformity, there are fewer points of contact between the components and hence, these points of surface contact are therefore subjected to higher bearing stresses and consequently higher wear rates. Advantageously, by increasing the conformity between the components it should be appreciated that lower bearing stresses are present and wear particle generation is decreased.

As a further result, the wear particulate burden imposed by the implant on the surrounding tissue is reduced following implantation. Consequently, the immune system response in the patient is reduced or possibly even eliminated, as is the associated inflammation, bone resorption and pain. Thus, patient comfort is increased. Additionally, as loosening of the implant from the destruction of the supporting bone is stimulated by wear particle mediated cytokine release from the immune system reactions of the patient, the loosening process is slowed thereby increasing the overall service life of the implant. In many applications, the resulting service life of the total joint implant will be extended for a sufficient period of time to allow the patient receiving the implant to avoid the need for revision surgery.

Similar to the pre-wearing steps of the method described above, the pre-implantation creeping may take place in a fluid bath or may be performed in an open air environment. In addition, it should be appreciated that the pre-implantation creeping may be performed either prior to, simultaneous with or following the pre-wearing or, the pre-implantation creeping may even be performed individually as the only process for reducing wear particulate generation.

More particularly, the pre-implantation creeping includes applying to the polymer component a pressure between 0.1–50.0 MPa. More preferably, the pressure applied to the polymer component is between 2–10 MPa when the total joint orthopaedic implant is to be used as a hip joint. Additionally, the applied pressure is preferably between 10–30 MPa when the total joint orthopaedic implant is to be used as a knee joint. These preferred ranges of pressures are selected to approximate the range of peak pressures expected to be placed upon the implant following implantation in the patient. Further, the pre-implantation creeping includes applying the pressure for a period between 100–10,000 minutes. Preferably, the pressure is applied for a period between 1000–8000 minutes and more preferably for a period of 3000–4000 minutes.

In accordance with yet another aspect of the pre-implantation creeping of the present invention, the creeping is performed at a temperature of between 18°–45° C. Preferably, the creeping is performed at a temperature of between 20°–40° C. and more preferably, at a temperature of between 20°–22° C. or 36°–38° C. The more preferred temperature range of 20°–22° C. designates a typical room temperature at which the pre-implantation creeping may be performed. In addition, the more preferred temperature range of 36°–38° C. represents an approximation of the temperatures that the implant would be subjected to in vivo. It should be appreciated that the creeping process requires less time and pressure when performed at higher temperatures.

In accordance with still another important aspect of the present invention, a total joint orthopaedic implant subjected to pre-implantation creeping in accordance with the present method is provided.

Still other objects of the present invention will become apparent to those skilled in this art from the following description wherein there is shown and described a preferred embodiment of this invention, simply by way of illustration of one of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWING

The accompanying drawing incorporated in and forming a part of the specification, illustrates several aspects of the present invention and together with the description serves to explain the principles of the invention. In the drawing.

Figure 1:
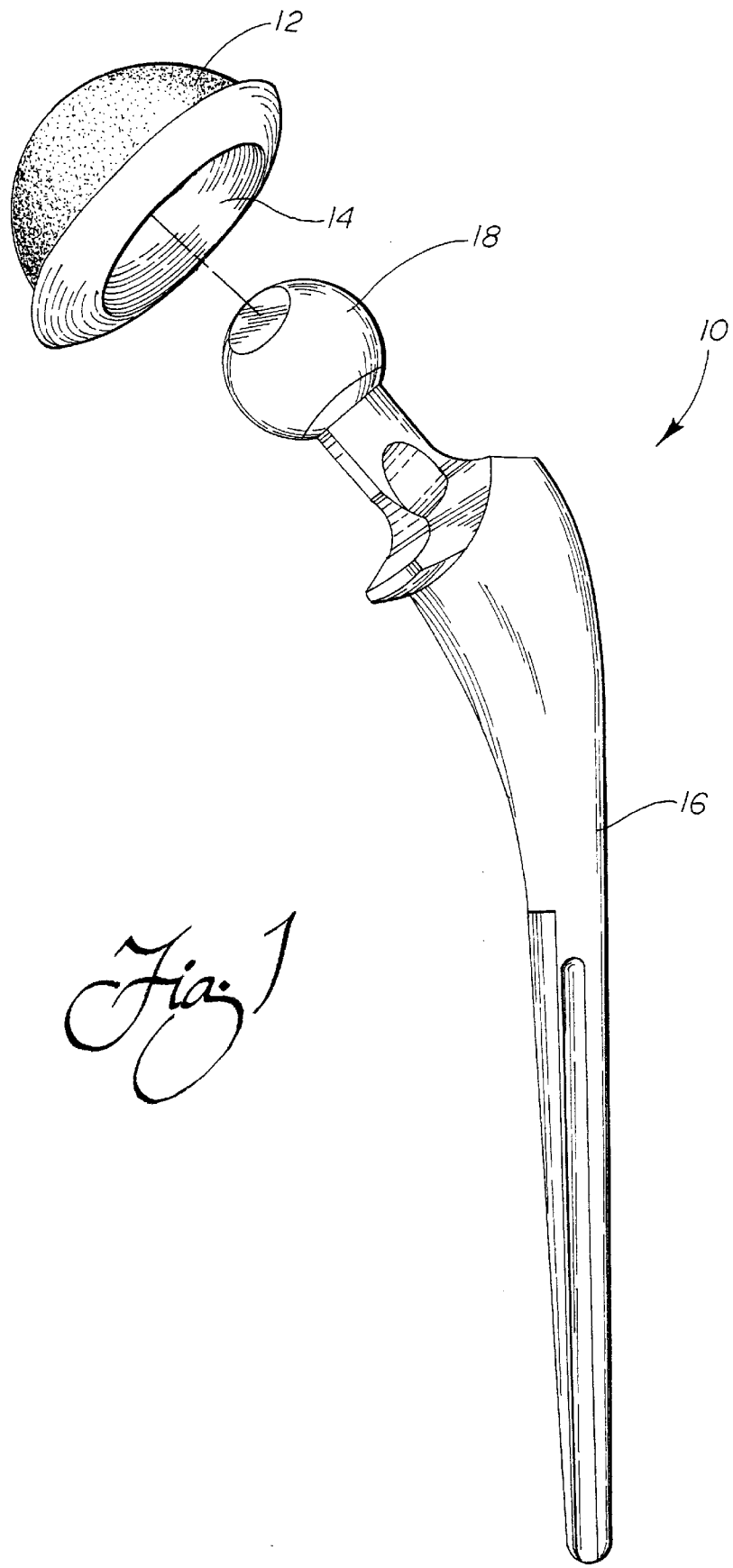
FIG. 1 is a perspective view showing a total joint orthopaedic implant processed in accordance with the present method.

Reference will now be made in detail to the present preferred embodiment of the invention, an example of which is illustrated in the accompanying drawing.

DETAILED DESCRIPTION OF THE INVENTION

The method for reducing the amount of wear particulates generated by a total joint orthopaedic implant system of two matched articulating components broadly comprises the steps of placing the total joint orthopaedic implant 10, including the acetabular cup or socket 12 with the concave polymer surface 14 and the femoral component 16 with the head 18 having a convex counterface formed from metal or ceramic, into a fluid bath. A hip implant is only represented for purposes of illustration. It should be appreciated that a total joint orthopaedic implant for the knee, elbow, shoulder, and ankle joints could also be processed in accordance with the present method.

Next, is the articulating of the implant in the fluid bath for at least 1,000 and more preferably at least 10,000 cycles. In accordance with this method, the total joint orthopaedic implant is pre-worn outside the body of the patient to remove laps, folds and other particulates and provide good surface-to-surface fit and polish so as to reduce the wear particulate burden imposed by the implant on surrounding tissue following implantation. This advantageously serves to increase the overall service life of the implant in a manner that is described in greater detail below.

More specifically, the method of the present invention is based upon the Archard equation:

$$T=kLV/H$$

wherein
T=rate of wear particle generation
k=a constant for a specific test system
L=load (or force)
V=sliding velocity of the two surfaces
H=material hardness.

In this equation, the value of the constant k depends on a number of factors including temperature, area of the wear interface, the fluid environment of the two matched articulating components, the surface finish, the number of wear cycles and other factors.

Still more specifically, the method of the present invention is particularly adapted to achieve a high precision fit and finish between the two articulating components so that the components are essentially matched to one another for smooth, low friction, low wear operation in vivo. Thus, the final fitting of the components is achieved external to the body in a specific controlled environment. Advantageously, this has a number of benefits over prior art procedures wherein modular, previously unmatched components are selected by the surgeon and are implanted in the patient. There final wearing in and precision fitting of the two surfaces are achieved but, unfortunately, the wear debris produced during initial removal of laps and folds is all delivered to the tissues at the expense of adverse biological side effects and reduced total joint implant service lifetime.

Specifically, wear particulates and debris are produced in the patient during the wearing in period in a manner that results in inflammation and problematic immune system response. This problem is substantially delayed or avoided by use of the present method of pre-wearing or breaking in outside of the body.

The present method also functions to establish a film layer on the cooperating load bearing surfaces of the matched articulating components. Advantageously, the film layer functions after implantation to provide smooth low friction operation of the implant while also minimizing wear for the overall benefit of the patient. Advantageously, by providing both a precision matched fit and a film layer, the present method effectively functions to smooth operation of the implant and also significantly reduce the generation of wear particulates and maximizes implant service life longevity.

Further, while some wear particulates are still likely to be produced over time, those produced are generally of smaller size so that they may be phagocytized by macrophages and transported away through the lymphatic system. Further, the volume or number of particulates produced are likely to be reduced sufficiently so that the lymphatic system is not overloaded. Thus, as a result of the present invention, an equilibrium state is achieved wherein no serious problematic immune system response leading to bone resorption and loosening of the implant is generated in the patient. As a result, the life of the implant is significantly increased and the risk of the patient having to undergo revision or replacement surgery is significantly reduced or eliminated. Of course, the inflammation and pain associated with and leading up to implant failure are also typically avoided.

In accordance with the more detailed aspects of the present invention the fluid in the fluid bath in which the implant is submerged during articulation has a viscosity of between 0.5–2000 times that of water. The solvent of the fluid bath may be water, and various solutes may be added, but in the later stages of the wearing in process the fluid is preferably selected from a group of fluids consisting of water, fetal calf serum, bovine serum, natural synovial fluid, synthetic synovial fluid and any mixtures thereof. Of course, the fluid bath may also include a relatively low concentration of preservatives or antimicrobial agents to prevent the growth of bacteria, fungi, or other microorganisms present in the fluid during implant processing.

To establish the film layer on the total joint orthopaedic implant, it is necessary to include a film layer forming solute in the fluid bath. Such a solute may, for example, be selected from a group consisting of polytetrafluoroethylene, hyaluronic acid, lubricin and any mixtures thereof. It should be appreciated, however, that these film layer solutes are only presented for purposes of example and that other such solutes may be utilized.

Generally, it is also preferred to drain the fluid from and replace the fluid in the fluid bath during the articulating and establishing steps. This advantageously, has the effect of replacing the film layer forming solutes as they are adsorbed and incorporated into the surfaces of the matched articulating components. Advantageously, by maintaining a higher concentration of film layer forming solutes in the fluid bath throughout the present method, it is possible to establish a more effective film layer particularly on the cooperating load bearing surfaces of the matched components.

Further, it is often desirable to filter the fluid in the fluid bath during the articulating of the matched components of the implant. In this way, particulates produced during articulation are removed from the fluid bath. Accordingly, these particulates are no longer present in the fluid to be drawn in between and through the relatively sliding load bearing surfaces of the implant where they could act as an abrasive and prevent the formation of the desired smooth, polished finish of those cooperating surfaces in the later stages of the present method.

Preferably, the method of the present invention is completed in multiple stages. In the first stage, the components of the implant are articulated under loads of between, for example, 0.1 to 500 Newtons at sliding surface velocities ranging from 0.1–0.5 meters per second. Some of these loads and sliding speeds are less than those to which the implant is expected to be subjected to following implantation in the patient. However, they are sufficient to remove the most pronounced laps and folds from the cooperating load bearing surfaces of the matched components. During this initial stage, it may also be desired to utilize water alone or only a very low viscosity lubricant in order to facilitate wear particle formation and removal of the lap and fold wear debris. Preferably, this first stage is performed for at least 100 cycles and, more preferably for a total of between 500–5000 cycles.

During a second stage of the method, higher load forces are applied. More specifically, load forces equaling or slightly exceeding those experienced during normal body movement are preferably utilized. Further, the load may be varied during articulating (e.g. in accordance with a square, triangular, sinusoidal or a Paul type curve) so as to simulate the load expected to be placed upon the implant by a patient during actual use following implantation. This is done for the purpose of causing local cold working and localized wear hardening on the wear surfaces. In this way, the hardness or wear resistance of the material surface is increased. This is desired to reduce the subsequent rate of wear of the implant following implantation. More specifically, during this second stage of articulation the implant is subjected to a load of between approximately 100–2500 Newtons and sliding surface velocities of between 0.01 and 0.5 meters per second. Again, this second stage of processing may be accomplished dry or in the presence of only a low viscosity lubricant such as water. This increases the speed of wear and hence, reduces processing times. This second stage of processing is also performed for at least 100 cycles and, more preferably for a total of 500–5000 cycles.

During a third stage of the wearing in process, loads are greatly increased in excess of that expected to be experienced during standard and normal gait of a patient at velocities equal to or greater than that experienced during normal gait. More specifically, during this third stage the implant may be articulated under loads between, for example, 2,500–10,000 Newtons at sliding surface velocities of between 0.5 and 2.0 meters per second. Third stage processing is preferably performed for at least 100 cycles and, more preferably for a total of 500–10,000 cycles.

The third stage of the method is completed in a fluid bath incorporating a film layer forming solute. The purpose of the third stage is to utilize relatively high loads and rapid sliding velocities to physically or chemically create a film layer on the load bearing surfaces of the matched components. More specifically, the elevated pressures and increased sliding velocities impart energy into the system that facilitates reaction of the lubricating solutes and solvents with the wear surfaces. The ultimate objective of this stage of the process is to insure the formation of a layer of film that will last throughout the lifetime of the implant. The high pressures and the sliding velocities also function to further increase the wear resistance of the bearing surfaces of the implant.

As a result of the incorporation of the film layer, smooth low friction sliding action of the implant following implantation is insured. Further, as a result of the increased wear resistance of the bearing surfaces at loads and sliding velocity speeds greatly exceeding those to which the implant will be subjected following implantation, particulate generation following implantation is significantly reduced so as to achieve the benefits previously described.

In accordance with still yet another aspect of the present invention, all the processing parameters relating to load, sliding velocities, lubricants and cycling frequencies may be customized to meet the needs of different patients into which the implants will eventually be implanted. Further, the wearing-in process may, of course, be completed unidirectionally or multi directionally. Indeed, specific processing procedures will be developed for customizing the implants to be received in patients of differing weights, heights, sexes, levels of activity, skeletal dimensions etc.

In addition to the method including the wearing-in or breaking-in of an implant as set forth above, the present method also includes pre-implantation creeping for increasing the wear resistance of a total joint orthopaedic implant. The pre-implantation creeping achieves similar beneficial results as set forth in detail above for the pre-wearing of an implant. It should be recognized that the pre-implantation creeping may be performed in conjunction with the pre-wearing as a further means for decreasing the generation of wear particulates or the pre-implantation creeping may be performed independently without pre-wearing to reduce the amount of wear particulate generation.

More particularly, pre-implantation creeping results in increased conformity between the individual components which make up the total joint orthopaedic implant. Currently available joint implants are proven to have low conformity which means that there is a significant mismatch in the finish and sphericity of the bearing surfaces between the individual components of the implant. This mismatch means that the individual components do not touch at all positions during normal operation of the implant joint. Thus, points of contact exist and these are subjected to concentrated loads, higher bearing stresses and consequently higher wear rates. If the conformity is increased between the bearing surfaces of the individual components, loads are more evenly distributed and this translates into lower bearing stresses and reduced generation of wear particles.

Advantageously, the pre-implantation creeping serves to effectively increase the conformity between the two components. More specifically, the method of pre-implantation creeping is preferably performed on the concave surface component of the total joint orthopaedic implant, which is preferably made of a polymer or other material with physical properties similar to polyethylene. The creeping causes a change in dimension of the concave polymer component as a result of being subjected to a pressure at a designated temperature over an extended period of time. The creeping of the polymer component increases the conformity between the concave and convex counterface surfaces and this increased conformity evenly distributes loads, reduces bearing stresses, and increases the wear resistance of the orthopaedic total joint bearing component.

In accordance with the more detailed aspects of the pre-implantation creeping, the creeping may take place in a fluid bath, similar to the pre-wearing, in which the viscosity of the fluid is between 0.5–2000 times that of water. The solvent of the fluid bath may be water, and various solvents may be added but the fluid is preferably selected from a group of fluids consisting of water, fetal calf serum, bovine serum, natural synovial fluid, synthetic synovial fluid or other solutes and any mixtures thereof. Of course, the fluid bath may also include other additions such as preservatives or antimicrobial agents to prevent the growth of bacteria, fungi or other microorganisms that might otherwise be present in the fluid during implant processing. Alternatively, the creeping may also be performed in an open air environment, i.e. not submerged in any type of fluid.

The amount of pressure to be applied during the pre-implantation creeping is dependent upon the material properties of the implant, or the desired final use for the total joint orthopaedic implant. More specifically, the pre-implantation creeping includes applying a pressure of between 0.1–50.0 MPa to the polymer component. The application of pressure may be at a constant level but more preferably is varied in a way to substantially correspond to that which the implant is expected to be subjected to following implantation.

If the implant is to be used as a hip joint, then the applied pressure is preferably between 2–10 MPa. This range of pressure approximates the actual peak pressure that the implant will be subjected to once it is implanted to replace a hip joint of the patient. If the implant is to be used as a knee joint, then the pressure to be applied is preferably between 10–30 MPa. Similarly, this pressure range approximates the peak pressure that the implant will experience following implantation as a knee joint. Thus, by applying a pressure which is approximately equivalent to the pressure that the polymer component, and more specifically, the total joint orthopaedic implant, will experience following implantation, the conformity of the components is increased.

As a result, wear particulate generation that would have otherwise occurred within the body absent pre-implantation creeping occurs outside the body where no harmful effects are produced. Further, the resulting increase in the conformity of the components prior to implantation insures better and more even distribution of loads and reduced bearing stresses. Consequently, the implant functions more smoothly and wear particulate generation after implantation is minimized. Thus, as pointed out above, implant service life is also increased.

In addition to the pressure that is applied to a particular polymer component, the time over which such pressure is applied is also an important factor to be considered. The pressure should be applied for a period of 100–10,000 minutes. Preferably, the pressure is applied for a period of between 1000–8000 minutes and more preferably for a period of 3000–4000 minutes. Further, the direction of application of the pre-implantation creeping is also important. Both unidirectional and multidirectional applications are possible.

The temperature at which the pre-implantation creeping is performed is also an important factor to be considered. The temperature at which the pressure is applied is typically between 18°–45° C. More preferably, the temperature is maintained between 20°–40° C. If the creeping is being conducted at normal room temperatures, then the preferred temperature range is 20°–22° C. This temperature could be maintained either in a fluid bath or in an open air environment. However, the creeping can also take place at a temperature preferably between 36°–38° C. in order to simulate the temperatures which the component will be exposed to in vivo. Accordingly, the appropriate temperature range can be selected for any given situation or desired result. It should be noted, however, that the temperature at which the creeping takes place should, of course, not exceed the melting point of the particular polymer or like type substance being used.

In summary, numerous benefits result from employing the concepts of the present invention. Advantageously, the present method of wearing-in or breaking-in an implant, as well as, the pre-implantation creeping represents a significant advance in the art. More specifically, pre-wearing is effective to remove laps and folds by physically abrading them away in the lubricant bath. This serves to increase bearing surface conformity thereby decreasing bearing stresses and reducing the rate of wear particulate generation following implantation. Further, pre-wearing establishes a film layer in the pre-worn "matched pair", of orthopaedic joint implant components.

Pre-implantation creeping is effective to remove laps and folds by visioelastically deforming the aspirates and reducing the voids. As a result the conformity of the bearing surfaces is increased. Further, the polymer structure may also be physically modified by this procedure in a manner that makes the polymer more wear resistant: that is, this procedure reduces the length and increases the diameter of the thin Nanofibril-sized filaments that connect the submicron-sized particles that comprise the polymer's microstructure. This increases the resistance of these thin microfibrils to fracture.

It is the fracture of these microfibrils that may cause the undesired release of the submicron-sized structures into the tissues that initiate the cascade of immune responses that lead to aseptic loosening. Accordingly, the tissue burden is relieved by the present procedure and the inflammation and pain that might otherwise develop over time are typically avoided. In fact, in many cases an implant processed in accordance with the present method will be received, and will wear, in an almost equilibrium state with the immune system of the patient. Accordingly, the life of the implant is significantly increased and in most cases complicated, costly and painful revision surgery may be avoided.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with breadth to which they are fairly, legally and equitably entitled.

We claim:

1. A total joint orthopaedic implant, comprising:
   a pair of matched articulating components wherein at least one of the matched articulating components is made of a polymer that is precreeped;
   said polymer components being precreeped by:
   placing the polymer component in a fluid bath wherein fluid in said fluid bath has a viscosity between 0.5–2000 times that of water and is selected from a group consisting of water, fetal calf serum, bovine serum, natural synovial fluid, synthetic synovial fluid and any mixtures thereof;
   subjecting the polymer component to pre-implantation creeping by applying to the polymer component a pressure of between 0.1–50 MPa;
   whereby the pre-implantation creeping causes increased wear resistance for the polymer component and improved conformity between the matched articulating components so as to reduce the wear particulate burden imposed by the total joint orthopaedic implant on surrounding tissue following implantation and thereby increase overall service life of the total joint orthopaedic implant.

2. A total joint orthopaedic implant, comprising:
   a pair of matched articulating components wherein at least one of the matched articulating components is made of a polymer that is precreeped;
   said polymer components being precreeped by:
   placing the polymer component in a fluid bath wherein fluid in said fluid bath has a viscosity between 0.5–2000 times that of water and is selected from a group consisting of water, fetal calf serum, bovine serum, natural synovial fluid, synthetic synovial fluid and any mixtures thereof;
   subjecting the polymer component to pre-implantation creeping by applying to the polymer component a pressure of between 0.1–50 MPa for a period of between 100–10,000 minutes;
   whereby the pre-implantation creeping causes increased wear resistance for the polymer component and improved conformity between the matched articulating components so as to reduce the wear particulate burden imposed by the total joint orthopaedic implant on surrounding tissue following implantation and thereby increase overall service life of the total joint orthopaedic implant.

3. A total joint orthopaedic implant, comprising:
   a pair of matched articulating components wherein at least one of the matched articulating components is made of a polymer that is precreeped;
   said polymer components being precreeped by:
   placing the polymer component in a fluid bath wherein fluid in said fluid bath has a viscosity between 0.5–2000 times that of water and is selected from a group consisting of water, fetal calf serum, bovine serum, natural synovial fluid, synthetic synovial fluid and any mixtures thereof maintained at a temperature of between 18°–45° C.;
   subjecting the polymer component to pre-implantation creeping by applying to the polymer component a pressure of between 0.1–50 MPa for a period of between 100–10,000 minutes;
   whereby the pre-implantation creeping causes increased wear resistance for the polymer component and improved conformity between the matched articulating components so as to reduce the wear particulate burden imposed by the total joint orthopaedic implant on surrounding tissue following implantation and thereby increase overall service life of the total joint orthopaedic implant.

4. A total joint orthopaedic implant, comprising:
   a pair of matched, pre-worn articulating components wherein at least one of the matched articulating components is made of a polymer that is precreeped;
   said polymer components being pre-worn and precreeped by:
   subjecting the total joint orthopaedic implant to pre-wearing outside the body of a patient by placing the total joint orthopaedic implant in a first fluid bath and articulating the total joint orthopaedic implant in the first fluid bath for a predetermined number of cycles;
   placing the polymer component of the total joint orthopaedic implant in a processing environment selected from a group consisting of air, the first fluid bath and a second fluid bath; and
   subjecting the polymer component to pre-implantation creeping;
   whereby the total joint orthopaedic implant is pre-worn outside the body of a patient to remove laps, folds, and other particulates and provide good surface-to-surface fit and polish, as well as, subjected to pre-implantation creeping resulting in increased wear resistance for the polymer component and improved conformity between the matched articulating components so as to reduce the wear particulate burden imposed by the total joint orthopaedic implant on surrounding tissue following implantation and thereby increase overall service life of the total joint orthopaedic implant.

5. The total joint orthopaedic implant of claim 4 wherein said polymer component is pre-worn by;
   cycling the total joint orthopaedic implant at 0.01–100 Hz;
   loading the total joint orthopaedic implant so as to carry a weight between 0.1–10,000 Newtons; and
   articulating the total joint orthopaedic implant at sliding speeds of between 0.01–2.0 meters per second.

6. A total joint orthopaedic implant, comprising:
   a pair of matched, pre-worn articulating components wherein at least one of the matched articulating components is made of a polymer that is precreeped;
   said polymer components being pre-worn and precreeped by:
   subjecting the total joint orthopaedic implant to pre-wearing outside the body of a patient by placing the total joint orthopaedic implant in a first fluid bath and articulating the total joint orthopaedic implant in the first fluid bath for a predetermined number of cycles;
   placing the polymer component in a first fluid bath or a second fluid bath wherein fluid in said first or second fluid bath has a viscosity between 0.5–2000 times that of water and is selected from a group consisting of water, fetal calf serum, bovine serum, natural synovial fluid, synthetic synovial fluid and any mixtures thereof;

subjecting the polymer component to pre-implantation creeping by applying to the polymer component a pressure of between 0.1–50 MPa;

whereby the total joint orthopaedic implant is pre-worn outside the body of a patient to remove laps, folds, and other particulates and provide good surface-to-surface fit and polish, as well as, subjected to pre-implantation creeping resulting in increased wear resistance for the polymer component and improved conformity between the matched articulating components so as to reduce the wear particulate burden imposed by the total joint orthopaedic implant on surrounding tissue following implantation and thereby increase overall service life of the total joint orthopaedic implant.

7. A total joint orthopaedic implant, comprising:

a pair of matched, pre-worn articulating components wherein at least one of the matched articulating components is made of a polymer that is precreeped;

said polymer components being pre-worn and precreeped by:

subjecting the total joint orthopaedic implant to pre-wearing outside the body of a patient by placing the total joint orthopaedic implant in a first fluid bath and articulating the total joint orthopaedic implant in the first fluid bath for a predetermined number of cycles;

placing the polymer component in said first fluid bath or a second fluid bath wherein fluid in said first or second fluid bath has a viscosity between 0.5–2000 times that of water and is selected from a group consisting of water, fetal calf serum, bovine serum, natural synovial fluid, synthetic synovial fluid and any mixtures thereof;

subjecting the polymer component to pre-implantation creeping by applying to the polymer component a pressure of between 0.1–50 MPa for a period of between 100–10,000 minutes;

whereby the total joint orthopaedic implant is pre-worn outside the body of a patient to remove laps, folds, and other particulates and provide good surface-to-surface fit and polish, as well as, subjected to pre-implantation creeping resulting in increased wear resistance for the polymer component and improved conformity between the matched articulating components so as to reduce the wear particulate burden imposed by the total joint orthopaedic implant on surrounding tissue following implantation and thereby increase overall service life of the total joint orthopaedic implant.

8. A total joint orthopaedic implant, comprising:

a pair of matched, pre-worn articulating components wherein at least one of the matched articulating components is made of a polymer that is precreeped;

said polymer components being pre-worn and precreeped by:

subjecting the total joint orthopaedic implant to pre-wearing outside the body of a patient by placing the total joint orthopaedic implant in a first fluid bath and articulating the total joint orthopaedic implant in the first fluid bath for a predetermined number of cycles;

placing the polymer component in said first fluid bath or a second fluid bath wherein fluid in said first or second fluid bath has a viscosity between 0.5–2000 times that of water and is selected from a group consisting of water, fetal calf serum, bovine serum, natural synovial fluid, synthetic synovial fluid and any mixtures thereof maintained at a temperature of between 36°–38° C.;

subjecting the polymer component to pre-implantation creeping by applying to the polymer component a pressure of between 0.1–50 MPa for a period of between 100–10,000 minutes;

whereby the total joint orthopaedic implant is pre-worn outside the body of a patient to remove laps, folds, and other particulates and provide good surface-to-surface fit and polish, as well as, subjected to pre-implantation creeping resulting in increased wear resistance for the polymer component and improved conformity between the matched articulating components so as to reduce the wear particulate burden imposed by the total joint orthopaedic implant on surrounding tissue following implantation and thereby increase overall service life of the total joint orthopaedic implant.

* * * * *